(12) United States Patent
Strobech

(10) Patent No.: US 7,470,263 B2
(45) Date of Patent: Dec. 30, 2008

(54) OSTOMY SYSTEM

(75) Inventor: Esben Strobech, Horsholm (DK)

(73) Assignee: Coloplast A/S, Humlebaek (DK)

( * ) Notice: Subject to any disclaimer, the term of this patent is extended or adjusted under 35 U.S.C. 154(b) by 46 days.

(21) Appl. No.: 10/591,438

(22) PCT Filed: Feb. 28, 2005

(86) PCT No.: PCT/DK2005/000136

§ 371 (c)(1),
(2), (4) Date: Sep. 1, 2006

(87) PCT Pub. No.: WO2005/082297

PCT Pub. Date: Sep. 9, 2005

(65) Prior Publication Data

US 2007/0219514 A1 Sep. 20, 2007

(30) Foreign Application Priority Data

Mar. 1, 2004 (DK) ............................... 2004 00350

(51) Int. Cl.
*A61F 5/44* (2006.01)
(52) U.S. Cl. .................. 604/336; 604/337; 604/338; 604/339; 604/330; 604/331; 604/333
(58) Field of Classification Search .................. 604/317, 604/323, 324, 326, 327, 331–333, 337–339, 604/341, 350, 355
See application file for complete search history.

(56) References Cited

U.S. PATENT DOCUMENTS

| | | | |
|---|---|---|---|
| 4,300,560 A * | 11/1981 | Steer et al. .................. 604/335 |
| 4,367,732 A | 1/1983 | Poulsen et al. | |
| 4,449,970 A | 5/1984 | Bevan et al. | |
| 4,710,183 A | 12/1987 | Steer | |
| 4,714,465 A | 12/1987 | Steer | |
| 4,816,027 A | 3/1989 | Gilchrist et al. | |
| 4,917,689 A * | 4/1990 | Coombes ..................... 604/338 |
| 5,051,259 A | 9/1991 | Olsen et al. | |
| 5,209,744 A | 5/1993 | Abe et al. | |
| 5,248,308 A * | 9/1993 | von Emster ................. 604/337 |
| 5,306,264 A | 4/1994 | Ferguson et al. | |

(Continued)

FOREIGN PATENT DOCUMENTS

CA 1 108 958 9/1981

(Continued)

*Primary Examiner*—Tatyana Zalukaeva
*Assistant Examiner*—Ilya Y Treyger
(74) *Attorney, Agent, or Firm*—Jacobson Holman PLLC

(57) ABSTRACT

An ostomy system for receiving bodily waste having a gas impermeable outer bag and a water impermeable inner bag enclosed within the outer bag, as well as a coupling system for attaching the bag to the body of a patient and for securing the outer bag in relation to the inner bag. The coupling system defines an orifice to enable bodily waste to be received by the inner bag and includes a barrier for preventing liquids and solid particles from passing from the inner bag to the outer bag, at least part of the barrier being permeable to flatus gasses. The barrier may be in the form of a foam. The outer bag has an outlet with a flatus filter for releasing flatus gases from the outer bag. An inner bag is provided, which maintains its physical integrity, e.g. its buoyancy, upon immersion in water.

20 Claims, 3 Drawing Sheets

U.S. PATENT DOCUMENTS

| | | |
|---|---|---|
| 5,423,782 A | 6/1995 | Wolrich |
| 5,426,782 A | 6/1995 | Shiga |
| 5,496,297 A | 3/1996 | Olsen |
| 5,591,144 A | 1/1997 | Smith et al. |
| 5,690,622 A | 11/1997 | Smith et al. |
| 5,690,623 A | 11/1997 | Lenz et al. |
| 5,714,225 A | 2/1998 | Hansen et al. |
| 5,785,695 A | 7/1998 | Sato et al. |
| 5,800,415 A | 9/1998 | Olsen |
| 5,840,073 A * | 11/1998 | Olsen ......................... 604/333 |
| 5,865,819 A | 2/1999 | Cisko, Jr. et al. |
| 5,938,647 A | 8/1999 | Smith |
| 6,171,594 B1 | 1/2001 | Nielsen |
| 6,231,553 B1 * | 5/2001 | Hulett ......................... 604/332 |
| 6,303,700 B1 | 10/2001 | Chen |
| 6,312,415 B1 | 11/2001 | Nielsen et al. |
| 6,437,038 B1 | 8/2002 | Chen |
| 6,451,883 B1 | 9/2002 | Chen et al. |
| 6,685,683 B1 | 2/2004 | Clok et al. |
| 6,902,551 B2 * | 6/2005 | Hansen et al. ............... 604/342 |
| 7,087,042 B2 * | 8/2006 | Montgomery ............... 604/342 |
| 2004/0064132 A1 | 4/2004 | Boehringer et al. |

FOREIGN PATENT DOCUMENTS

| | | |
|---|---|---|
| DE | 1 947 368 | 4/1971 |
| DE | 195 19 069 A | 11/1996 |
| DE | 199 21 555 A1 | 2/2000 |
| DE | 203 08 266 U1 | 8/2003 |
| DE | 20 2004 000 323 U1 | 5/2004 |
| EP | 0 259 184 B1 | 3/1988 |
| EP | 0 320 895 A1 | 6/1989 |
| EP | 0 703 762 B1 | 4/1996 |
| EP | 0 747 026 B1 | 12/1996 |
| EP | 0 768 848 B1 | 4/1997 |
| EP | 0 768 849 B1 | 4/1997 |
| EP | 0 821 925 B1 | 2/1998 |
| EP | 1 290 994 A2 | 3/2003 |
| FR | 2 476 481 A1 | 8/1981 |
| GB | 2 265 832 A | 10/1993 |
| GB | 2 306 889 A | 5/1997 |
| HU | 190 848 | 11/1986 |
| WO | WO 91/01118 | 2/1991 |
| WO | WO 91/01119 | 2/1991 |
| WO | WO 93/18725 | 9/1993 |
| WO | WO 94/12128 | 6/1994 |
| WO | WO 94/18919 | 9/1994 |
| WO | WO 96/01090 | 1/1996 |
| WO | WO 99/30652 | 6/1999 |
| WO | WO 00/30576 | 6/2000 |
| WO | WO 00/54820 | 9/2000 |
| WO | WO 00/67683 | 11/2000 |
| WO | WO 01/05340 A2 | 1/2001 |
| WO | WO 01/10363 A1 | 2/2001 |
| WO | WO 01/21115 A1 | 3/2001 |
| WO | WO 01/54632 A1 | 8/2001 |
| WO | WO 01/82846 A1 | 11/2001 |
| WO | WO 02/058603 A1 | 8/2002 |
| WO | WO 2004/082452 A2 | 9/2004 |

* cited by examiner

OSTOMY SYSTEM

This is a nationalization of PCT/DK2005/000136 filed 28 Feb. 2005 and published in English.

TECHNICAL FIELD

The present invention relates to ostomy systems for bodily waste. More particularly, the invention concerns improvements to ostomy bag systems comprising an inner bag which may be flushed down a W.C. and an outer, protective bag which is not soiled with bodily waste and can be disposed of with household refuse.

BACKGROUND OF THE INVENTION

A large number of ostomy bags for receiving bodily waste from colostomy or ileostomy patients have been proposed in the prior art, cf. for example EP 0 259 184 and EP 703 762. The problem of conveniently and hygienically disposing the used bag has been addressed by several prior art documents, cf. for example EP 703 762, which discloses an inner bag made sufficiently water-impermeable to prevent leakage into the outer bag during the period of use, though—because of the existence of the outer bag—the inner bag need not be made from such durable material. Accordingly, the inner bag is made from a material which is water-impermeable over a short period, but which gradually dissolves over a more extended time period, such as from a biodegradable material. The inner bag is said to be of a structure which is weakened upon immersion in a WC bowl such that it becomes limp and is less buoyant thereby enabling it to be flushed away easily. The inner bag is enclosed within an outer bag which is formed from a material which acts as a barrier to flatus gasses and which is provided with a flatus filter. The inner bag is permeable to flatus gasses, so that such gasses may diffuse through walls of the inner bag into the outer bag, from which the flatus gasses escape through the flatus filter.

SUMMARY OF THE INVENTION

It has been found that the inner bag of the drainage bag of EP 703 762 does not instantaneously become limp and less buoyant upon immersion into a WC bowl. More specifically, such changes in limpness and buoyancy may occur over a period of some seconds up to several minutes, during which period obnoxious smells keep diffusing out of the walls of the inner bag. Moreover, already when the outer bag is removed, and the inner bag, which is at least partially filled with bodily waste, is to be disposed of, flatus gasses diffusing through the walls of the gas permeable walls of the inner bag tend to spread obnoxious smells.

It has hitherto been accepted that biodegradable ostomy bags should be become limp and less buoyant as rapidly as possible upon immersion into a WC bowl, so as to ensure a swift disintegration of the bags and thereby allow the bags to be flushed away easily. It has, however, been found that such a rapid dissolving of the bags pose a purification problem at water purifying plants, as partially or completely dissolved bag material is difficult to efficiently remove from sewage. Additionally, the relatively rapid sinking of known bags, as they become limp and less buoyant, may delay a user's disposing of the inner bag, because sinking does not occur immediately upon immersion into a WC bowl. As discussed above, it may take from a few seconds up to several minutes for a bag to become limp and less buoyant. While a user could flush the bag away immediately upon immersion thereof into a WC bowl, it has been found that users do in fact await sinking of the bag before flushing it away. The delay thereby caused results in ostomy patients spending more time than necessary at toilet facilities.

Preferred embodiments of the present invention seek to provide an ostomy system which at least partially solves some of the odour, cleaning and disposing problems discussed above.

Accordingly, the invention provides, in a first aspect, an ostomy system for receiving bodily waste, comprising:
- a gas impermeable outer bag;
- a water impermeable inner bag enclosed within the outer bag;
- a coupling system for attaching the bag to the body of a patient and for securing the inner bag in relation to the patient's body and for securing the outer bag in relation to the inner bag, the coupling system defining an orifice to enable bodily waste to be received by the inner bag;

characterised in that
- the coupling system comprises a barrier for preventing liquids and solid particles from passing from the inner bag to the outer bag, at least part of the barrier being permeable to flatus gasses;
- the outer bag is essentially made from a material which is impermeable to flatus gasses;
- the outer bag comprises an outlet with a flatus filter for releasing flatus gasses from the outer bag.

In a second aspect, the invention provides an ostomy system for receiving bodily waste, comprising:
- an outer bag;
- a water impermeable inner bag enclosed within the outer bag;
- a coupling system for mounting the bag to the body of a patient and for securing the inner bag in relation to the patient's body and for securing the outer bag in relation to the inner bag, the coupling system defining an orifice to enable bodily waste to be received by the inner bag;

characterised in that the inner bag is of a structure which essentially maintains its physical integrity upon immersion in water. In the present context, maintenance of the physical integrity of the inner bag preferably reflects that the bag does not dissolve, i.e. that it retains its structure as one single unbroken entity. It is preferred that the structure of the inner bag is such that the limpness of the inner bag remains essentially unaffected when the bag is immersed in water at e.g. at most 30° C., such as at 25° C.

Preferably, flatus gasses may escape only from the inner bag to the outer bag via the coupling system. In other words, the inner bag may be impermeable to flatus gasses, such impermeability being achieved, for example, by a material for the inner bag which is impermeable to flatus gasses. Accordingly, once the inner bag has been detached from the coupling system, flatus gasses may only escape from the inner bag through a faeces inlet opening thereof, through which faeces has entered the bag. As the inner bag is impermeable to flatus gasses, no such gasses escape via the walls of the bag. To minimize the escape of gas from the inner bag during the disposing process, a user may seal the faeces inlet opening of the inner bag prior to disposing the bag into a WC bowl, such sealing being, e.g., achieved by the user tying a knot in the inner bag or simply by folding and/or pressing portions of the wall material in the area of the faeces inlet opening.

The barrier of the coupling system may comprise a gas permeable foam and optionally also a gas permeable membrane, such as a hydrophobic gas permeable membrane. The foam and the optional membrane serve as the barrier to liquids and solid particles while allowing flatus gasses to pass therethrough. It will be understood that the actual choice of foam and membrane is a matter of selecting among commercially available products with the required gas permeability and particle/liquid impermeability characteristics. To provide a deodorizing effect, the foam may include activated carbon. While liquid may normally penetrate into the foam, though not all the way through the foam, provided the foam is sufficiently dense and/or sufficiently thick, the membrane is normally liquid proof. Thus, it is usually desirable to include a membrane in embodiments, in which the coupling system is to withstand large quantities of liquid, or in which the travelling distance through the foam is so small that a risk of liquid penetrating through the foam exists.

To ensure that flatus gasses travel a predetermined minimum distance within the foam, the barrier may comprise means for forcing the flow of flatus gasses in the barrier along a predetermined flow path. For example, there may be provided a sheet of a plastics material, e.g. PVC, in the foam, the sheet preventing flatus gasses from being conveyed along the shortest, i.e. straight-line route from the inlet to the foam to the outlet thereof. The sheet may e.g. extend along a substantial part of the periphery of the coupling, such as for example along ½ to ⅚ of the periphery. Alternatively, there may be provided a junction, e.g. a welding, at which an outer and an inner flange of the coupling system, between which there is provided the foam, are joined, whereby flatus gasses in the foam are prevented from flowing across the junction.

As discussed above, the present inventors have found that a rapid dissolving of the bags pose a purification problem at water purifying plants. More specifically, it has been found that the process of purifying sewage is less complicated in case such sewage contains bags which are not entirely dissolved than in case the sewage contains completely dissolved bags. This is due to the fact those parts of a bag which are not entirely dissolved may be easily removed from the sewage by appropriate mechanical means, such as simple filters, whereas those entirely dissolved parts have to be removed by more sophisticated purification processes. This problem is addressed by providing a structure of the inner bag which allows the inner bag to essentially maintain its physical integrity upon immersion in water.

The structure may be such that the inner bag does not loose its physical integrity and/or limpness and/or buoyancy immediately upon immersion in water or shortly thereafter. Preferably, the material of the inner bag should be such that it essentially maintains its physical integrity and/or limpness and/or buoyancy upon immersion in water at at most 30° C., such as 25° C., for at least 10 minutes, preferably for at least 1 hour, such as for at least 6 or at least 12 hours, such as for at least 24 hours, preferably for at least 36 hours, and more preferably for at least 48 hours. Most preferably, the inner bag maintains its physical integrity at a purifying plant or in a septic tank for at least 1 week, such as for 1-4 weeks. This has several advantages. Firstly, it facilitates a user's handling of a used bag to be flushed away, as the user will not wait for what may appear as an inconveniently long time from placing a used ostomy bag in a WC bowl until the bag has lost its buoyancy, has changed its limpness or lost its physical integrity, at which time the user usually decides to flush away the bag. Once the user has become used to a bag which does not become less buoyant or changes limpness or looses its physical integrity upon immersion in a WC bowl, he or she will not wait at the WC bowl for the bag to sink or disintegrate, and accordingly the user needs to spend less time at the WC bowl. Secondly, as the inner bag maintains its physical integrity for an extended period of time, it does not dissolve before reaching a purification plant together with the sewage which conveys the bag, and accordingly it may easily be filtered out of the sewage in a water purification process.

Preferably, the material of the inner bag is biodegradable. In preferred embodiments, the material of the inner bag comprises a mix of starch, such as maize or potato starch, and polyester, such as synthetic polyester, such as polycaprolactone. It has been found that such a material combines the qualities of being soft, i.e. providing a low level of rustle noise when worn by a user, flexible, and being capable of maintaining its physical integrity upon immersion in water. For example, the material of the inner bag may comprise 35-55%, such as 40-50% by weight of starch and 35-55%, such as 40-50% by weight of the synthetic polyester. In one embodiment, the material of the inner bag comprises starch and synthetic polyester in substantially equal ratios. In order to soften the inner bag and to improve wearing comfort, the inner bag may comprise 10% or less by weight of a softener, such as glycerol.

In one embodiment, the inner bag is made from a material of the above composition, the material being essentially insoluble in water. The material may be hygroscopic to such a degree that it absorbs 10-25% by weight of water, such as 15-18%. The water permeability of the material may be between 3000 and 4000 g per $m^2$ per day, and the biodegradability may be such that 10-20 μm of the material thickness is degraded after 2-3 weeks in still water at 25° C. Preferably, the material of the inner bag fulfils ISO standards for biodegradability.

One suitable material for the inner bag is the commercially available Mater-Bi NF01U supplied by Novamont SpA, Novara, Italy.

The coupling system is preferably one which comprises a body flange to be attached to the patient's body, with a central opening through which bodily waste may be received. The gas permeable barrier may be provided in the form of a ring-shaped member attached to an outer surface of the body flange, said outer surface of the body flange facing away from the patient's body during use of the ostomy system, the ring-shaped barrier thereby defining a central opening which coextends with the central opening of the body flange. On an outer surface of the barrier, i.e. on that surface facing away from the patient's body, there may be provided an outer flange defining a central opening which coextends with the central opening of the body flange and of the barrier. The inner bag may in this case be sealed to an outer surface of the outer flange, so that flatus gasses may only escape from the inner bag to the outer bag through the barrier.

In one embodiment, the outer flange overlaps the barrier, whereby respective radially inwardly facing rim portions of the body flange, the barrier and the outer flange define a boundary of the orifice through which bodily waste may enter the inner bag. Thereby, the flatus gasses enter the barrier through the radially inwardly facing rim portion thereof.

In all embodiments of the invention, the barrier may comprise a foam. The foam may thus, for example, constitute or be comprised in the ring-shaped member comprised in the embodiments discussed above. Alternatively, an outer surface of the foam may be provided with a gas-impermeable surface layer, in which case the inner bag may be sealed to the outer surface of the surface layer and arranged such that a first portion of the outer surface of the coated barrier faces the interior of the inner bag, and such that a second portion of the outer surface of the coated barrier faces the exterior of the inner bag. In other words, one portion of the surface layer faces the inner bag, and another portion thereof faces the outer bag. To allow flatus gasses to enter the foam, the surface layer may comprise at least one perforation allowing flatus gasses to enter the barrier at the first portion thereof and to exit the barrier at the second portion thereof, whereby flatus gasses may escape from the inner bag. The at least one perforation may be provided as a single perforation extending between the two portions of the surface layer or, alternatively, there may be provided at least two distinct perforations, at least one of which is in one of the two portions of the surface layer, and at least one of which is in the other one of the two surface portions. The perforation or perforations may be provided as one or more non-coated outer surface portion of the barrier.

As discussed above, there may be provided means in the foam for forcing the flatus gasses to flow along a predetermined flow path within the foam, so as to ensure that flatus gasses diffusing from the inner bag into the outer bag travel a predetermined minimum distance within the foam. Such means may e.g. be in the form of a radially extending obstruction. In one embodiment, there is provided an inlet to the foam through which flatus gasses enter the foam, and a foam outlet through which flatus gasses emerge from the foam, the inlet and outlet being angularly displaced with respect to one another. If no obstruction is provided, flatus gasses travel the shortest possible distance between the perforations. However, by providing an obstruction which may, e.g., extend in a radial direction across the foam at a location blocking the shortest possible flow path between the two perforations, it may be ensured that flatus gasses travel the longest distance between the perforations. One convenient way of providing the obstruction is to force the outer surface layer of the foam to adhere to a backing of the foam, e.g. a surface of the body flange, such as by welding the outer surface layer to the backing or by gluing the parts together.

BRIEF DESCRIPTION OF THE DRAWINGS

The invention will now be further described with reference to the drawings, in which.

DETAILED DESCRIPTION OF THE DRAWINGS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
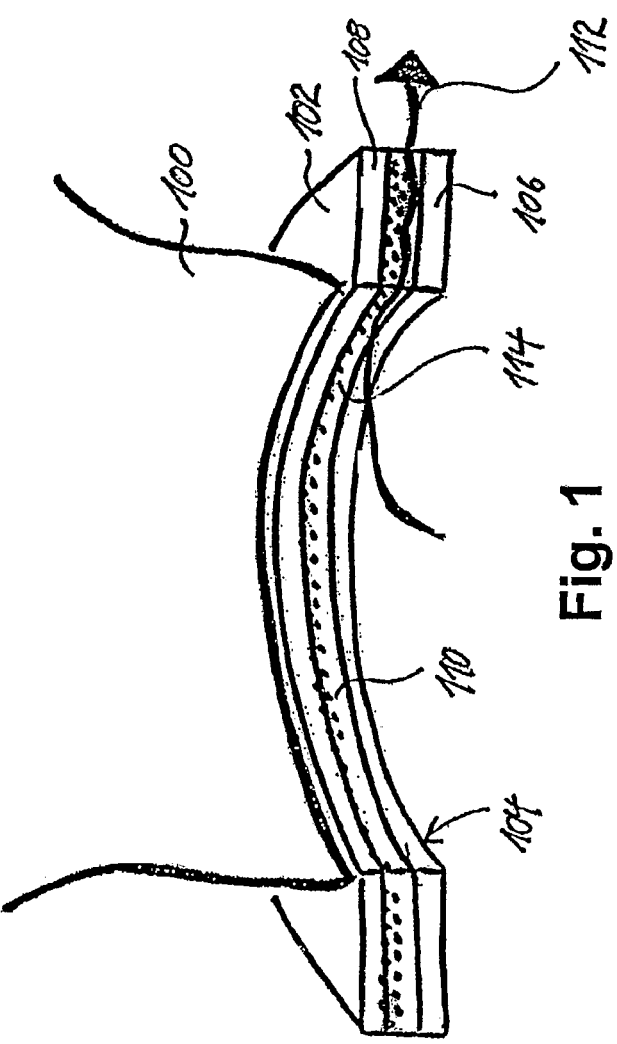
FIG. 1 shows a partial cross-section through a portion of a first embodiment of an ostomy system according to the invention, with a barrier to liquids and solid particles being sandwiched between a body flange and an outer flange.
Figure 2:
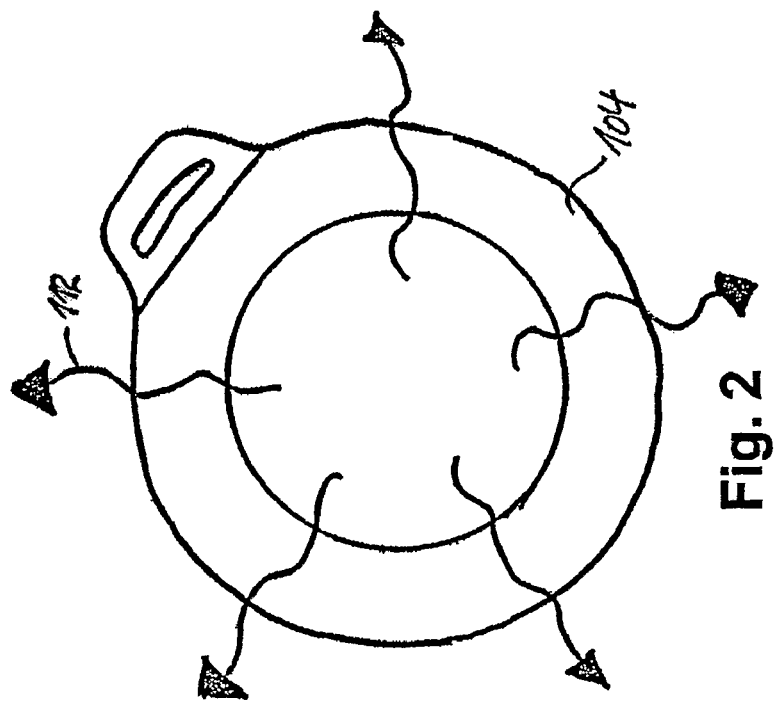
FIG. 2 is an end view illustration of the embodiment of FIG. 1.

FIG. 1 shows a partial view of an ostomy system embodying the first and second aspects of the invention. The ostomy system comprises a water and gas impermeable inner bag 100 attached to an outer surface portion 102 of a coupling system 104. The coupling system has a body flange 106 and an outer flange 108, between which there is sandwiched a barrier to liquid and solid particles in the form of a foam 110. An outer bag (not shown) is attached to the coupling system. As indicated by arrows 112 in FIGS. 1 and 2, flatus gasses entering the inner bag may diffuse through the foam 110 into the outer bag, the flatus gasses entering the foam through an inwardly facing rim portion 114 thereof. The outer bag is preferably provided with a flatus filter, such as a conventional activated carbon filter.

Figure 3:
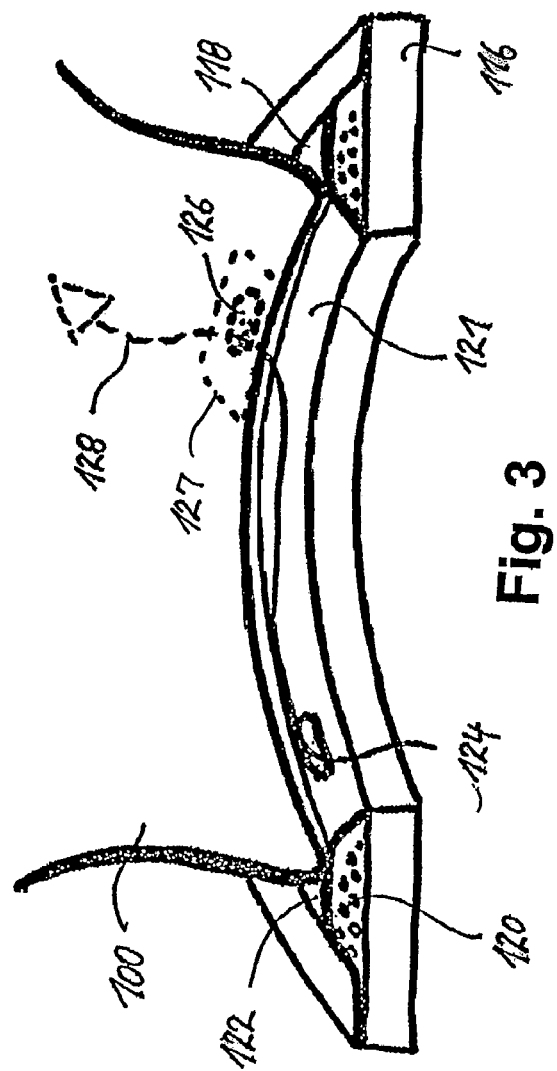
FIG. 3 shows a partial cross-section through a second embodiment of an ostomy system according to the invention, with a barrier to liquids and solid particles being attached to an outer surface of a body flange.

FIG. 3 illustrates an alternative embodiment of an ostomy system embodying both aspects of the invention. The system comprises a water and gas impermeable inner bag 100 attached to an elevated surface portion 118 of body flange 116. The elevated surface portion is constituted by a barrier in the form of a foam 120 appropriately covered by a water impermeable surface layer 121 of, e.g., latex rubber or a plastic film. An inlet perforation 124 in the surface layer allows flatus gasses to enter the foam, the flatus gasses exiting the foam through an outlet perforation 126, as indicated by arrow 128. The perforations are arranged such that the inlet perforation 124 faces the interior of the inner bag, and such that the outlet perforation 126 faces the exterior of the inner bag, but yet the interior of the outer bag (not shown), which in turn is preferably provided with a flatus filter. Outlet perforation 126 may optionally be provided with a gas permeable, hydrophobic membrane 127.

Figure 4:
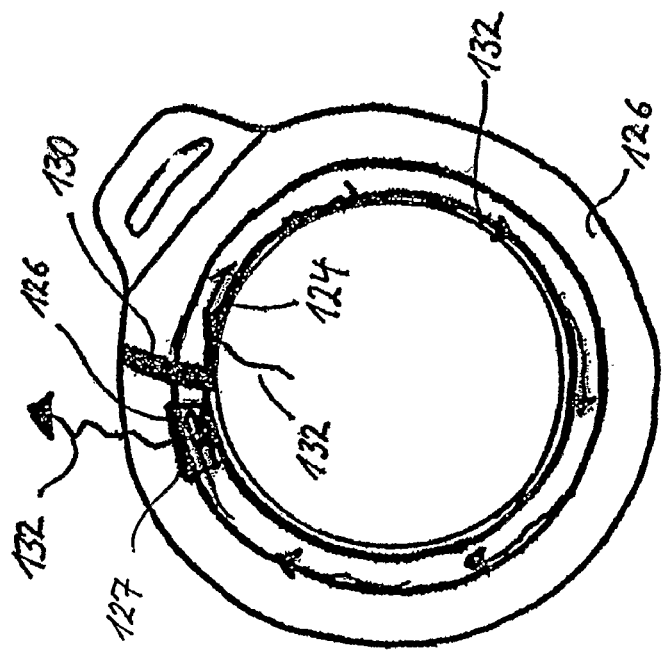
FIG. 4 is an end view illustration of an embodiment in which there is provided means for forcing the flow of flatus gasses in the barrier along a predetermined flow path.

FIG. 4 illustrates a similar embodiment with perforations 124 and 126 provided at the interior and exterior of the inner bag 100, respectively. A welding 130 joining the surface layer 121 to the body flange 116 prevents flatus gasses and possibly liquid from flowing counter clockwise in the foam 120 from the inlet perforation 124 to the outlet perforation 126. As illustrated by arrows 132, liquid and gasses travel clockwise in the foam along a distance through the foam which is significantly longer than the shortest, straight-line distance between the perforations. As a result of the extended travelling distance, liquid and solid particles deposit in the foam, and only gasses escape the foam into the outer bag (not shown) via outlet perforation 126.

Figure 5:
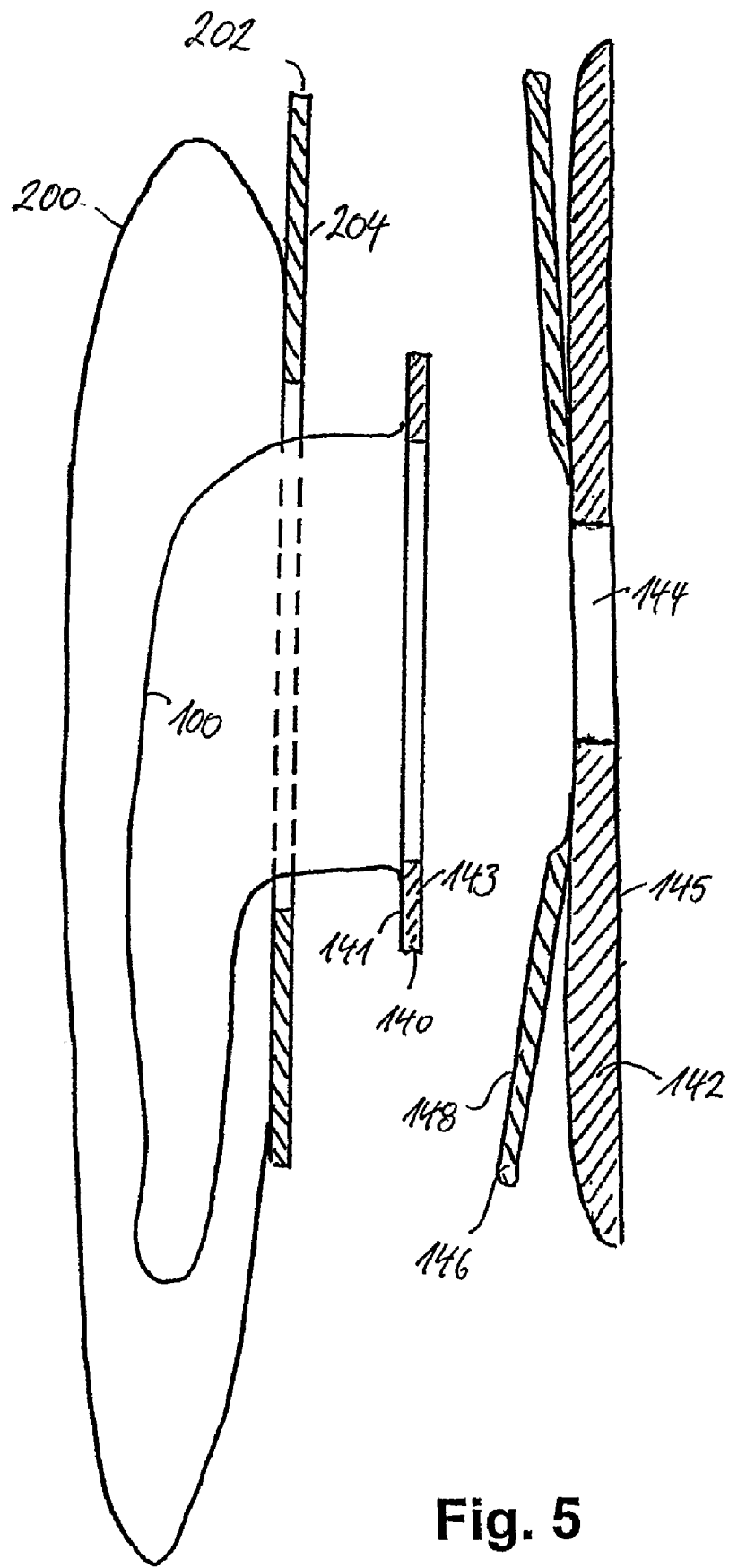
FIG. 5 illustrates an embodiment of an ostomy system according to the invention.

FIG. 5 generally illustrates an ostomy system comprising inner bag 100 and an outer bag 200. The outer bag is supported by an outer flange 202 defining a surface 204 for attachment to surface 148 of supporting flange 146. The supporting flange 146 is secured to body flange 142, which defines an opening 144 for receiving the stoma of a patient and a mounting surface 145 provided with a hydrocolloid adhesive for attaching the system to the body of the patient. The inner bag 100 is supported by flange 140, which defines a first surface 141 for attachment to surface 204 of the outer flange 202, and a second opposite surface 143 for attachment to surface 148 of supporting flange 146. The adhering properties of the respective surfaces of outer flange 202, flange 140 and supporting flange 146 are such that surface 141 adheres stronger to surface 204 than the surface 143 adheres to the surface 148. Accordingly, when the patient dismounts outer flange 202 from supporting flange 146, flange 140 disengages from supporting flange 146, while flange 140 remain attached to outer flange 202. Subsequently, flange 140 and inner bag 100 may be removed from outer flange 202. Inner bag 100 and flange 140 may, as described above, be flushed down a toilet bowl, whereas outer bag 200 and outer flange 202 may be disposed of with household refuse.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. An ostomy system for receiving bodily waste, comprising:
   a gas impermeable outer bag;
   a water impermeable inner bag enclosed within the outer bag;
   a coupling system for attaching the bag to the body of a patient and for securing the inner bag in relation to the patient's body and for securing the outer bag in relation to the inner bag, the coupling system defining an orifice to enable bodily waste from a stoma to be received by the inner bag, said coupling system including,
      a body flange configured to be attached to the patient's body, the body flange defining a central opening with an inwardly facing rim portion;
      an outer flange defining a central opening with an inwardly facing rim portion; and
      a barrier for preventing liquids and solid particles from passing from the inner bag to the outer bag, at least part of said barrier being permeable to flatus gases, said barrier being in the form of a ring-shaped member defining a central opening with an inwardly facing rim portion, said ring-shaped barrier being sandwiched between the body flange and the outer flange such that the respective radially inwardly facing rim portions of the body flange, the barrier and the outer flange define a boundary of the orifice so that the flatus gases enter the barrier through the radially inwardly facing rim portion thereof; and
   the inner bag being sealed to an outer surface of the outer flange so that flatus gases may only escape from the inner bag through the barrier, and the gas impermeable outer bag being arranged such that flatus gases escaping the inner bag through the barrier enter the outer bag, said outer bag including an outlet with a flatus filter for releasing flatus gases from the outer bag to the environment.

2. The ostomy system according to claim 1, wherein the inner bag is impermeable to flatus gases.

3. The ostomy system according to claim 1, wherein the barrier includes a gas permeable foam.

4. The ostomy system according to claim 1, wherein the barrier includes a gas permeable membrane.

5. The ostomy system according to claim 1, wherein the barrier is configured to force the flow of flatus gases in the barrier along a predetermined flow path.

6. The ostomy system according to claim 1, wherein the inner bag is of a structure which essentially maintains its physical integrity upon immersion in water.

7. The ostomy system according to claim 1, wherein the barrier includes a foam, at least an outer surface of which is provided with a gas-impermeable surface layer;
   the inner bag being sealed to the outer surface of the surface layer, so that a first portion of the outer surface of the coated barrier faces the interior of the inner bag, and so that a second portion of the outer surface of the coated barrier faces the exterior of the inner bag;
   the surface layer including at least one perforation allowing flatus gases to enter the barrier at the first portion thereof and to exit the barrier at the second portion thereof, whereby flatus gases may escape from the inner bag;
   the outer bag being arranged such that flatus gases escaping the inner bag through the barrier enter the outer bag.

8. The ostomy system according to claim 7, wherein said at least one perforation is provided as a non-coated outer surface portion of the barrier which extends partially into said first portion of the outer surface of the barrier and partially into said second portion.

9. The ostomy system according to claim 7, wherein said at least one perforation is provided as a plurality of distinct perforations, at least one of which is provided at said first portion of the outer surface of the barrier, and at least another one of which is provided at said second portion.

10. The ostomy system according to claim 9, wherein the perforation at said first portion of the outer surface of the barrier is angularly displaced with respect to the perforation at said second portion, the barrier including a partial obstruction to flatus gases that is arranged between the perforation in the first portion and the perforation in the second portion, so that flatus gases are conveyable in one and only one angular direction between said perforations.

11. An ostomy system for receiving bodily waste, comprising:
    a gas impermeable outer bag;
    a water impermeable inner bag enclosed within the outer bag;
    a coupling system defining an orifice to enable bodily waste from a stoma to be received by the inner bag, said coupling system including a body flange configured to be attached to the patient's body and having a central opening with an inwardly facing rim portion, an outer flange having a central opening with an inwardly facing rim portion, and a ring-shaped barrier member having a central opening with an inwardly facing rim portion, said barrier member having at least a part thereof that is permeable to flatus gases and being sandwiched between the body flange and the outer flange to prevent liquids and solid particles from passing from the inner bag to the outer bag, the respective radially inwardly facing rim portions of the body flange, the barrier and the outer flange defining a boundary of the orifice so that the flatus gases enter the barrier through the radially inwardly facing rim portion thereof; and
    the inner bag being sealed to the outer flange so that flatus gases may only escape from the inner bag through the barrier, and the gas impermeable outer bag being arranged such that flatus gases escaping the inner bag through the barrier enter the outer bag and exit therefrom through a filtered outlet in said outer bag.

12. The ostomy system according to claim 11, wherein the inner bag is impermeable to flatus gases.

13. The ostomy system according to claim 11, wherein the barrier includes a gas permeable foam.

14. The ostomy system according to claim 11, wherein the barrier includes a gas permeable membrane.

15. The ostomy system according to claim 11, wherein the barrier is configured to force the flow of flatus gases in the barrier along a predetermined flow path.

16. The ostomy system according to claim 11, wherein the inner bag is of a structure which essentially maintains its physical integrity upon immersion in water.

17. The ostomy system according to claim 11, wherein the barrier includes a foam, at least an outer surface of which is provided with a gas-impermeable surface layer;
    the inner bag being sealed to the outer surface of the surface layer, so that a first portion of the outer surface of the coated barrier faces the interior of the inner bag, and so that a second portion of the outer surface of the coated barrier faces the exterior of the inner bag;
    the surface layer including at least one perforation allowing flatus gases to enter the barrier at the first portion thereof, and to exit the barrier at the second portion thereof, whereby flatus gases may escape from the inner bag;

the outer bag being arranged such that flatus gases escaping the inner bag through the barrier enter the outer bag.

18. The ostomy system according to claim 17, wherein said at least one perforation is provided as a non-coated outer surface portion of the barrier which extends partially into said first portion of the outer surface of the barrier and partially into said second portion.

19. The ostomy system according to claim 17, wherein said at least one perforation is provided as a plurality of distinct perforations, at least one of which is provided at said first portion of the outer surface of the barrier, and at least another one of which is provided at said second portion.

20. The ostomy system according to claim 19, wherein the perforation at said first portion of the outer surface of the barrier is angularly displaced with respect to the perforation at said second portion, the barrier including a partial obstruction to flatus gases that is arranged between the perforation in the first portion and the perforation in the second portion, so that flatus gases are conveyable in one and only one angular direction between said perforations.

* * * * *